US011191607B2

(12) United States Patent
Szuchmacher

(10) Patent No.: US 11,191,607 B2
(45) Date of Patent: Dec. 7, 2021

(54) OPERATING ROOM LIGHTING SYSTEM

(71) Applicant: Mauricio Szuchmacher, Coram, NY (US)

(72) Inventor: Mauricio Szuchmacher, Coram, NY (US)

(*) Notice: Subject to any disclaimer, the term of this patent is extended or adjusted under 35 U.S.C. 154(b) by 84 days.

(21) Appl. No.: 16/701,655

(22) Filed: Dec. 3, 2019

(65) Prior Publication Data

US 2020/0246103 A1 Aug. 6, 2020

Related U.S. Application Data

(60) Provisional application No. 62/801,200, filed on Feb. 5, 2019.

(51) Int. Cl.
*A61B 90/30* (2016.01)
*F21L 14/04* (2006.01)
*F21S 8/00* (2006.01)
*F21S 8/04* (2006.01)
*F21V 21/32* (2006.01)
(Continued)

(52) U.S. Cl.
CPC .............. *A61B 90/30* (2016.02); *A61B 90/08* (2016.02); *A61B 90/35* (2016.02); *A61B 90/361* (2016.02); *F21L 4/08* (2013.01); *F21L 14/04* (2013.01); *F21S 8/033* (2013.01); *F21S 8/046* (2013.01); *F21V 21/145* (2013.01); *F21V 21/32* (2013.01); *F21V 21/403* (2013.01); *F21V 21/406* (2013.01); *A61B 2090/308* (2016.02);
(Continued)

(58) Field of Classification Search
CPC ......... A61B 90/30; A61B 90/08; A61B 90/35; A61B 90/361; A61B 2090/308; A61B 2560/0487; F21L 4/08; F21L 14/04; F21S 8/033; F21S 8/046; F21V 21/145; F21V 21/32; F21V 21/403; F21V 21/406; F21W 2131/205
USPC .................................................. 362/640, 804
See application file for complete search history.

(56) References Cited

U.S. PATENT DOCUMENTS 4,597,030 A 6/1986 Brody et al.
4,975,826 A * 12/1990 Bell ........................ A61C 19/00
16/421
(Continued)

FOREIGN PATENT DOCUMENTS

CA 2465524 A1 * 5/2003 ........... A61G 12/004

*Primary Examiner* — Laura K Tso

(57) ABSTRACT

A flexible operating room lighting system may be coupled to a wall, ceiling, or fixture of a facility. The lighting system can modularly accommodate multiple illumination arms and incorporate one or more microphone thereon, permitting the vocal control using a processor for hands free operations. The lighting system may include a speaker and a camera to facilitate two-way communications with a user to facilitate demonstrations for individuals undergoing tutelage in the particular facility's profession. The lighting system may employ a stand with wheels to facilitate modularity. Further, a cover with a transparent front end may be provided to be slipped over the lighting system and securing through a cover fastener. By providing each illumination arm with a jack, the illumination arm may be modularly assigned, replaced, sanitized. Thus, the present invention provides reliable sanitary measures while further facilitating a flexible operable device through the illumination arms.

8 Claims, 8 Drawing Sheets

(51) Int. Cl.

| | |
|---|---|
| *F21V 21/14* | (2006.01) |
| *F21V 21/40* | (2006.01) |
| *A61B 90/35* | (2016.01) |
| *A61B 90/00* | (2016.01) |
| *F21L 4/08* | (2006.01) |
| *F21W 131/205* | (2006.01) |

(52) U.S. Cl.
CPC ............ *A61B 2560/0487* (2013.01); *F21W 2131/205* (2013.01)

(56) References Cited

U.S. PATENT DOCUMENTS

| | | | |
|---|---|---|---|
| 5,353,786 A | 10/1994 | Wilk | |
| 6,874,908 B2 | 4/2005 | Sharrah et al. | |
| D568,528 S * | 5/2008 | Hood | A61B 90/30 D26/119 |
| 7,581,864 B2 * | 9/2009 | Craig | A61C 19/066 362/573 |
| D632,413 S | 2/2011 | Teufel et al. | |
| 9,587,792 B1 * | 3/2017 | Parsons | F16M 11/2092 |
| 9,967,936 B2 * | 5/2018 | Wood | A61B 90/30 |
| 10,231,799 B1 * | 3/2019 | Kalava | F21V 3/04 |
| 10,436,426 B2 * | 10/2019 | Thomas | F21L 14/04 |
| 2004/0090776 A1 | 5/2004 | Yang | |
| 2006/0102811 A1 * | 5/2006 | Musset | F16M 11/24 248/121 |
| 2010/0030033 A1 | 2/2010 | Farley et al. | |
| 2014/0221754 A1 * | 8/2014 | Cabaud | A61B 1/0684 600/178 |
| 2019/0199915 A1 * | 6/2019 | Coiseur | G06K 9/3208 |

\* cited by examiner

OPERATING ROOM LIGHTING SYSTEM

The current application claims a priority to the U.S. Provisional Patent application Ser. No. 62/801,200 filed on Feb. 5, 2019.

FIELD OF THE INVENTION

The present invention relates generally to lighting systems. More specifically, the present invention relates to a modular lighting system that is particularly employed for intraoperative settings.

BACKGROUND OF THE INVENTION

Optimal quality lighting is critical for any medical facility, no matter if it is an ER (emergency room), an OR (operating room), a trauma bay, a surgical office, or an exam room in a doctor's office. This applies to dentist offices as well, for dental implants, and veterinary surgery rooms for large or small animals. All medical, dental, and veterinary professionals need excellent lighting when providing care.

Presently, lighting is known to the art, as are lighting arrangements in an intraoperative/surgical setting where the lighting requires frequent manipulation and sterilization considerations. Conventional intraoperative lighting generally invokes a bulky lighting system that is tedious to manipulate once a procedure is underway. Many existing surgical lights do have drawbacks.

For example, mounted surgical lights that are ceiling or wall-mounted do provide plenty of light, but they do lack some degree of flexibility. No matter how much light they produce, they are still fixed at their base. They may have quite a reach, but they cannot be moved into the next room. Additionally, it is very important to mount the light source exactly where it will be needed and at the correct height. Any redesign of the facility layout or furniture can cause the mounted light device to be unusable. Further, a light source should be arranged appropriately so that a patient lying in an exam chair or on an examination table is not staring directly into the bright light.

On the other hand, many existing portable surgical lights are likely to get in the way of the medical professionals as they perform the procedure. The light source would then need to be moved, or at least slightly adjusted any time the patient has a positional change, or the doctor needs to see from a different angle. Additionally, most portable surgical lights do not provide the flexibility to easily adjust the surgical lamp head for optimal viewing of the surgical site. Tracking a portable surgical light's location and making sure it is available for a procedure are common problems. There is always the possibility that a portable surgical light will be in another room when it is needed, or it is unavailable because it is already in use.

It is therefore the objective of the present invention to introduce a lighting system that in a first embodiment may be coupled to an extraneous ceiling, connected to a conventional power grid of the facility through a base. Whereupon the base a plurality of ports is disposed that may accommodate an equal number of illumination arms to be modularly coupled therein. Additionally, the illumination arm may be guided into a particular orientation and direction by a handle along the illumination arm. Further, the illumination arm may comprise an optional microphone thereon, permitting the vocal control of the illumination means as executed by a processor within the base. An illumination head located at the distal end of the illumination arm opposite the jack and base side may further accommodate thereon a speaker and a camera. Thus, the present invention may facilitate two-way communications by the speaker with an extraneous personal computing (PC) device, or even facilitate demonstrations for individuals undergoing tutelage in the particular facility's profession. Further, the present invention may employ a stand that further facilitates modularity of the apparatus by permitting motion along a plurality of wheels and controls localized to a stand casing atop a column and a plurality of legs/wheels. Further still, a cover may be provided to the at least one illumination arm. Wherein the illumination arm having a smaller volume than traditional intraoperative/surgical/medical lighting, permits the tubular cover to be slipped over the at least one illumination arm, and securing through a cover fastening means. Thus, the present invention provides reliable sanitary measures aligned to standard conventions, while further facilitating a smaller operable device through the illumination arms, and the direction of the illumination head may be manipulated through the handle. Additionally, by providing the illumination arm with a jack that compliments an individual port of the plurality of ports, the illumination arm may be modularly assigned, replaced, sanitized, and added as the situation demands in a capacity extensively more expedient than conventional overhead assemblies. Further, by providing the microphone alongside a processor, the present invention may facilitate hands free operations, furthering the sanitary measures of the present invention while simultaneously affording two-way communications and educational operations through the optional speaker and the optional camera.

SUMMARY OF THE INVENTION

A flexible operating room lighting system is designed to be coupled to an extraneous wall, ceiling, or fixture, and connected to a conventional power grid of a medical, dental, or veterinary facility. Through a solid base, the flexible lighting system can accommodate multiple illumination arms to be modularly coupled therein. By adapting the solid base to existing mounting mechanisms used to mount lights on ceilings, walls, and fixtures of intraoperative facilities, the flexible lighting system can be used to conveniently and efficiently replace existing conventionally lighting systems. Additionally, each illumination arm is flexible, thus can be guided into a particular orientation and direction. By providing the illumination arm with a jack that compliments an individual port of a plurality of ports on the base, the illumination arm may be modularly assigned, replaced, sanitized, and added as the situation demands in a capacity extensively more expedient than conventional overhead systems.

Each illumination arm may comprise one or more microphone thereon, permitting the vocal control of the illumination arm as executed by a processor of the flexible lighting system. By providing the microphone alongside the processor, the flexible lighting system may facilitate hands free operations, offering sanitary measures of the flexible lighting system. A speaker and a camera can be installed on the illumination arm to facilitate two-way communications with an extraneous personal computing (PC) device, or even facilitate demonstrations for individuals undergoing tutelage in the particular facility's profession. The flexible lighting system may employ a stand that further facilitates modularity of the apparatus by permitting motion along a plurality of wheels and controls localized to a stand casing atop a column and a plurality of legs/wheels.

Further, a cover with a transparent front end may be provided to the at least one illumination arm of the flexible lighting system. Since the illumination arm has a smaller volume than traditional intraoperative, surgical, and/or medical lighting, the flexible lighting system permits the tubular cover to be slipped over the at least one illumination arm and securing through a cover fastener. Thus, the flexible lighting system provides reliable sanitary measures aligned to standard conventions, while further facilitating a smaller operable device through the illumination arms.

DETAIL DESCRIPTIONS OF THE INVENTION

Figure 1:
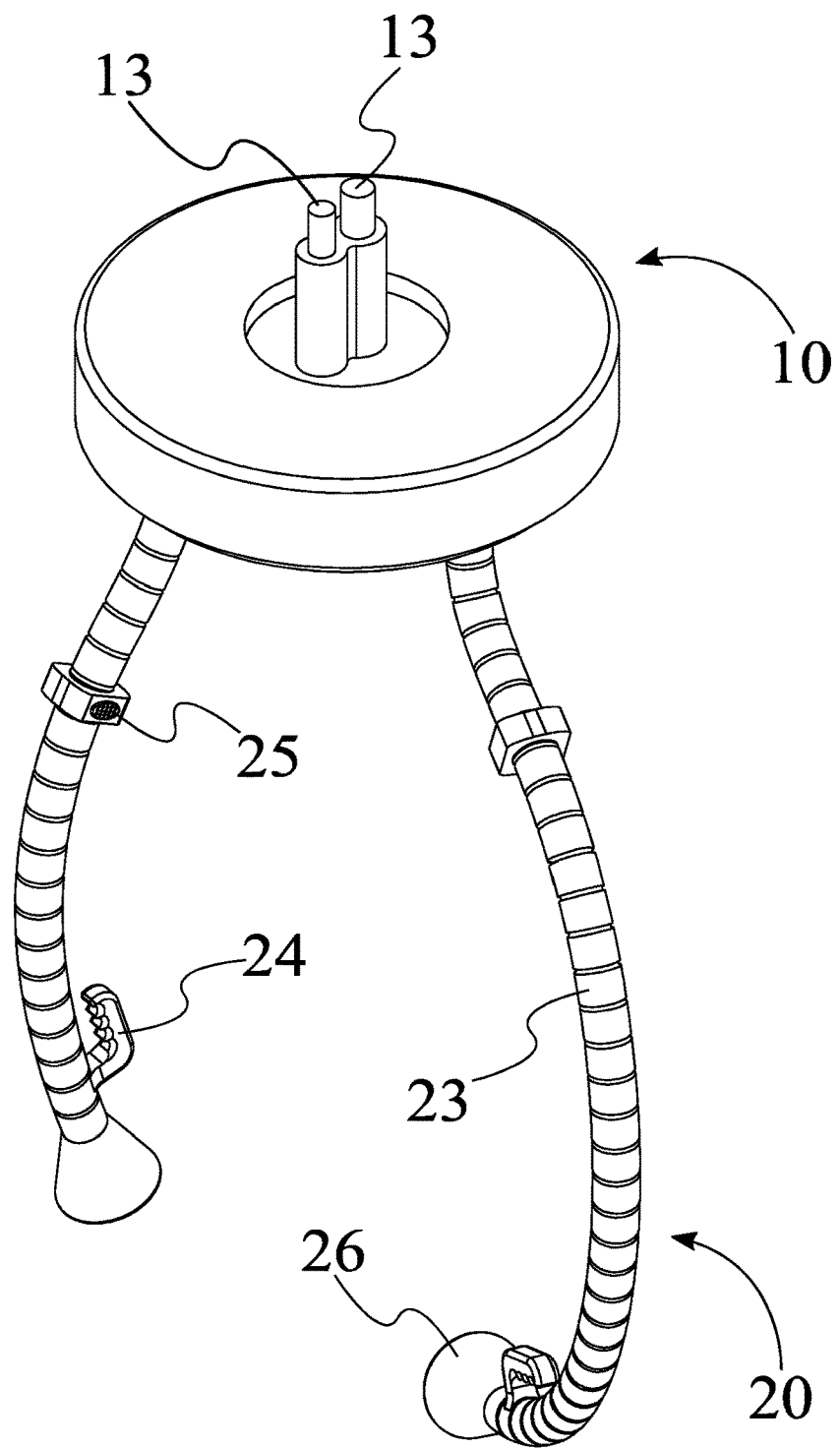
FIG. 1 is a perspective view of the preferred embodiment of the present invention, where the base is observed with the plurality of cables protruding from the top surface thereof.
Figure 2:
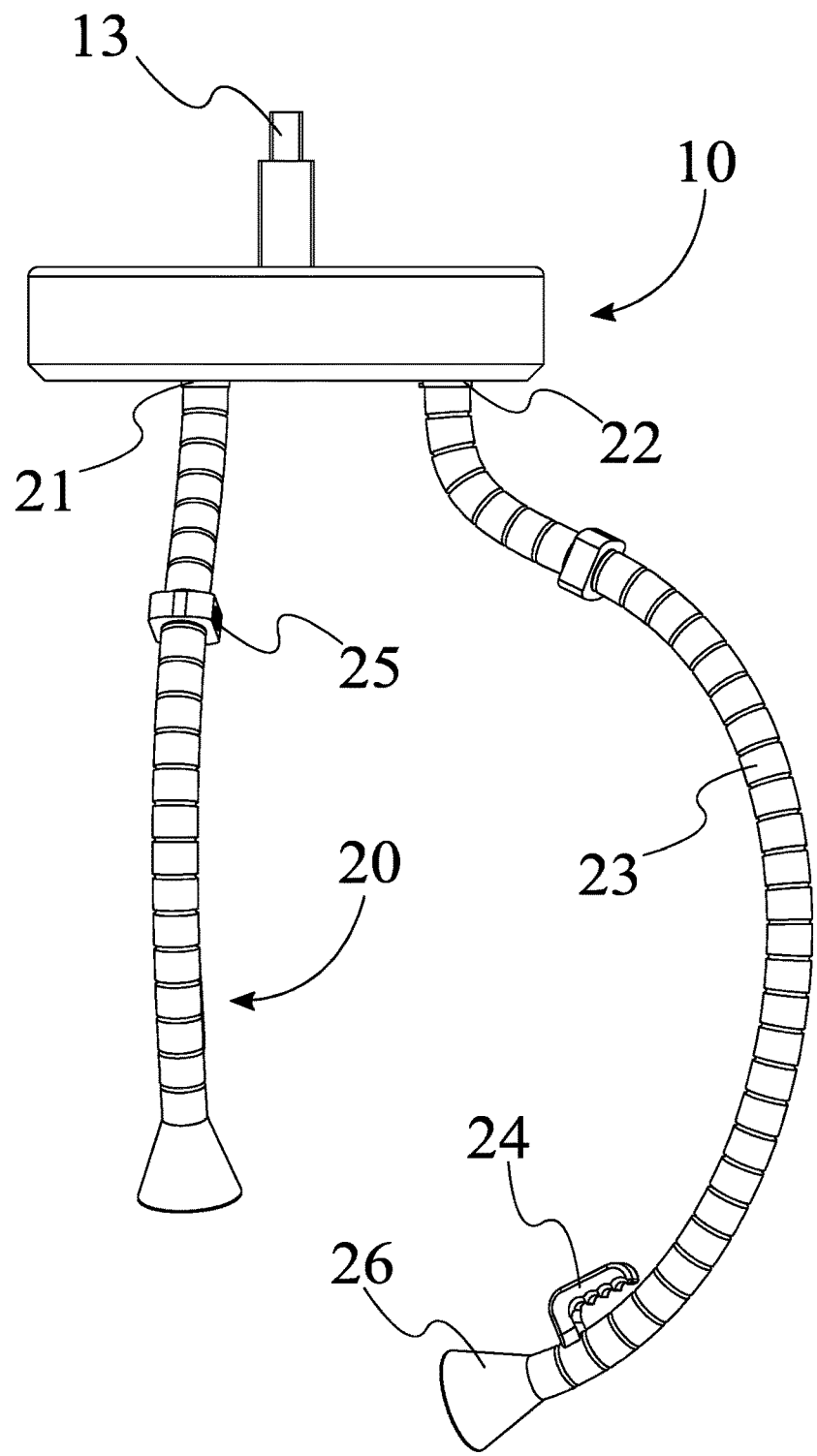
FIG. 2 is a front view of the present invention, wherein the jack base is observed flush with the underside of the base and at the distal end of the arm.
Figure 3:
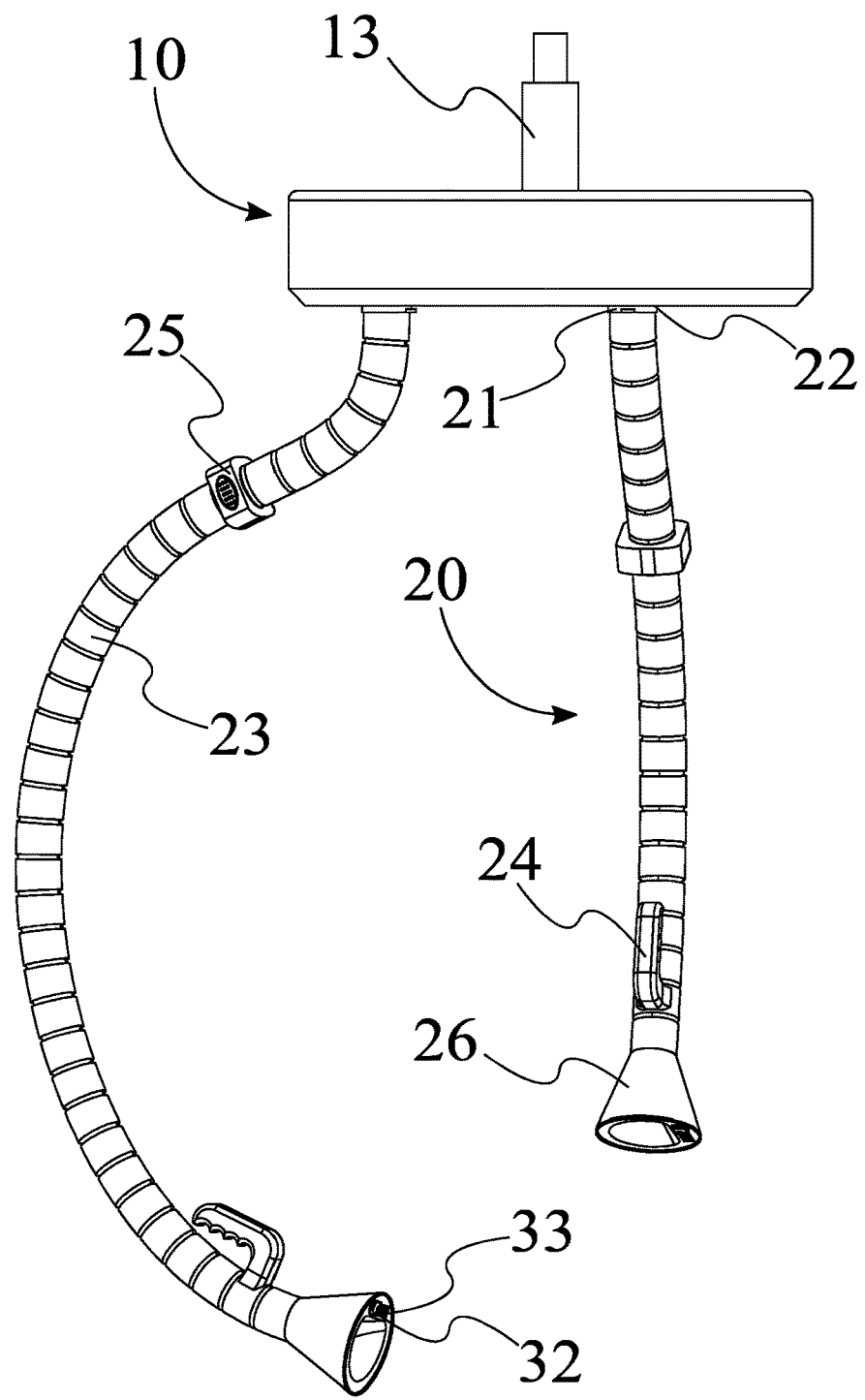
FIG. 3 is a rear view of the present invention, wherein the microphone is observed along the arm between the jack base and the handle.
Figure 4:
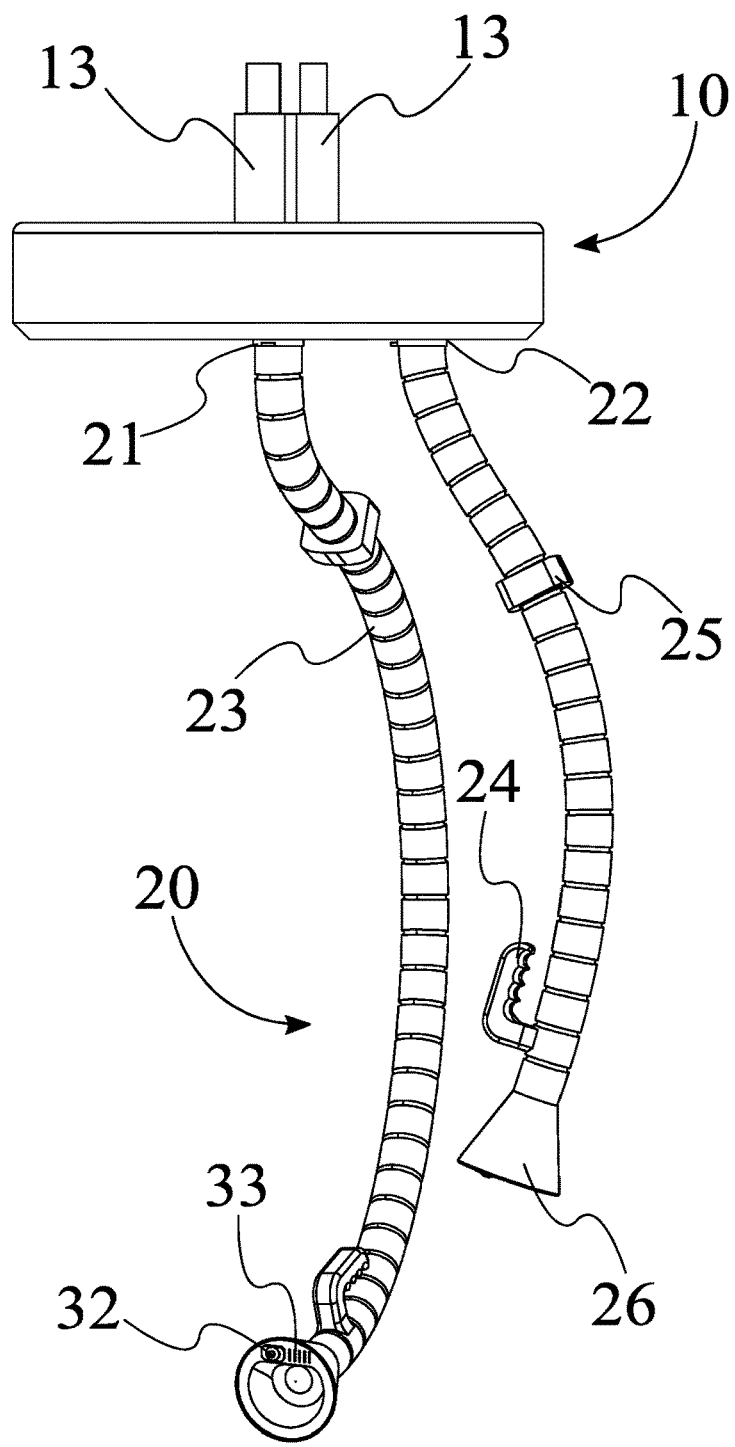
FIG. 4 is a right view of the present invention.
Figure 5:
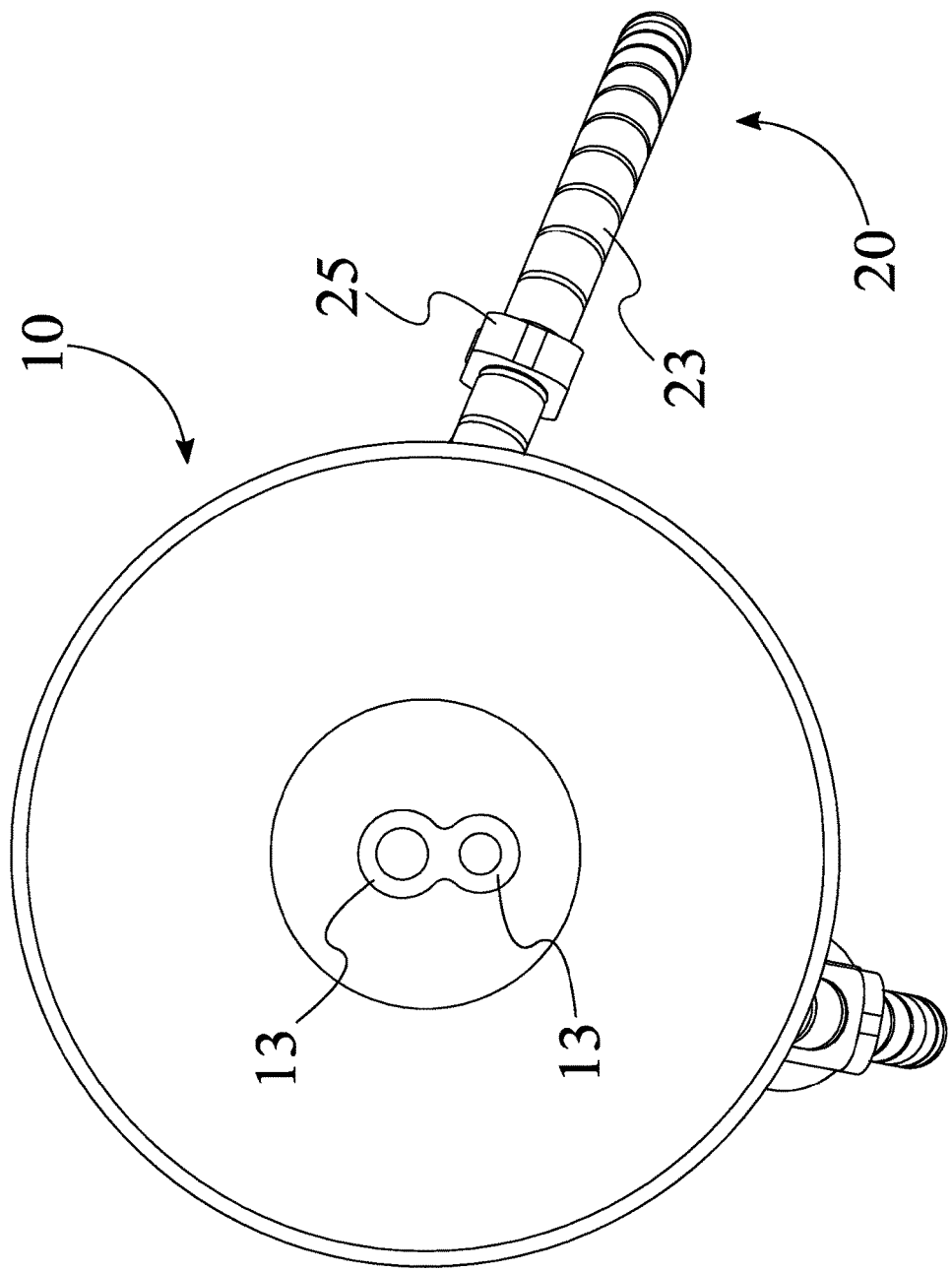
FIG. 5 is a top view of the present invention.

All illustrations of the drawings are for the purpose of describing selected versions of the present invention and are not intended to limit the scope of the present invention.

As can be seen in FIG. 1 to FIG. 8, the present invention provides an operating room lighting system that may be coupled to an extraneous wall, ceiling, or fixture, and connected to a conventional power grid of the facility. The lighting system can accommodate multiple illumination arms to be modularly coupled therein. Additionally, each illumination arm of the present invention is flexible, thus can be guided into a particular orientation and direction the illumination arm. Further, the illumination arm may comprise one or more microphone thereon, permitting the vocal control of the illumination arm as executed by a processor. The present invention may further accommodate a speaker and a camera installed on the illumination arm to facilitate two-way communications with an extraneous personal computing (PC) device, or even facilitate demonstrations for individuals undergoing tutelage in the particular facility's profession. Further, the present invention may employ a stand that further facilitates modularity of the apparatus by permitting motion along a plurality of wheels and controls localized to a stand casing atop a column and a plurality of legs/wheels. Further, a cover with a transparent front end may be provided to the at least one illumination arm, wherein the illumination arm having a smaller volume than traditional intraoperative, surgical, and/or medical lighting, permits the tubular cover to be slipped over the at least one illumination arm, and securing through a cover fastener.

Thus, the present invention provides reliable sanitary measures aligned to standard conventions, while further facilitating a smaller operable device through the illumination arms. Additionally, by providing the illumination arm with a jack that compliments an individual port of a plurality of ports, the illumination arm may be modularly assigned, replaced, sanitized, and added as the situation demands in a capacity extensively more expedient than conventional overhead assemblies. Further, by providing the microphone alongside the processor, the present invention may facilitate hands free operations, furthering the sanitary measures of the present invention while simultaneously affording two-way communications and educational operations through the speaker camera.

As can be seen in FIG. 1 to FIG. 5, the present invention comprises a flexible lighting system for medical, dental, and veterinary facilities. More specifically, the flexible lighting system of the present invention comprises a base 10 and at least one illumination arm 20, which is detachably attached to the base 10. The base 10 comprises a plurality of ports 11, a processor 12, a plurality of cables 13, a relay 14, a power source 17, an extraneous power source 15, and an extraneous personal computing (PC) device 16. The plurality of ports 11 is terminally positioned on the base 10, and the plurality of cables 13 is terminally positioned on the base 10 opposite the plurality of ports 11. The at least one illumination arm 20 comprises a jack 21, an arm 23, a microphone 25, an illumination head 26, a camera 32, a speaker 33, and a plurality of wires. The illumination head 26 is terminally positioned on the arm 23 while the jack 21 is terminally positioned on the arm 23 opposite the illumination head 26. Additionally, the jack 21 is mounted to one of the plurality of ports 11 of the base 10. The at least one illumination arm 20 is detachably attached to the base 10 through the jack 21, and the illumination head 26 of the at least one illumination arm 20 is connected to an external power source 15 through the plurality of cables 13 of the base 10. In the preferred embodiment of the present invention, the base 10 is cylindrical in shape and accommodating the at least one illumination arm 20 thereon. The base 10 is attached to a ceiling, a wall, or a fixture, by extraneous fasteners or coupling elements that permit the flexible lighting system to be anchored to a particular location overhead of an environment. Although the base 10 is preferably cylindrical, the base 10 may be alternative geometries including, but not limited to, cubic rectilinear, trilinear, domed, arcuate, polygonal, and so on. Additionally, the base 10 may be configured to be installed on an existing light fixture base for retrofitting and/or remodeling purposes. This feature allows a user to efficiently change out an existing lighting system to the present invention.

As can be seen in FIG. 1 to FIG. 5, the plurality of ports 11 is positioned on at least one planar or arcuate surface of the base 10. The individual ports of the plurality of ports 11 accommodate the individual illumination arm 20 through the jack 21 thereof. Each port of the plurality of ports 11 is in connection with the processor 12 through the plurality of cables 13 spanning through the base 10. Further, the plurality of ports 11 comprises at least three individual ports that are further preferably arranged radially equidistant in the exemplified embodiment. However, a lower or higher count of individual ports of the plurality of ports 11 is feasible to accommodate any number of arms 23 of the at least one illumination arm 20.

Figure 6:
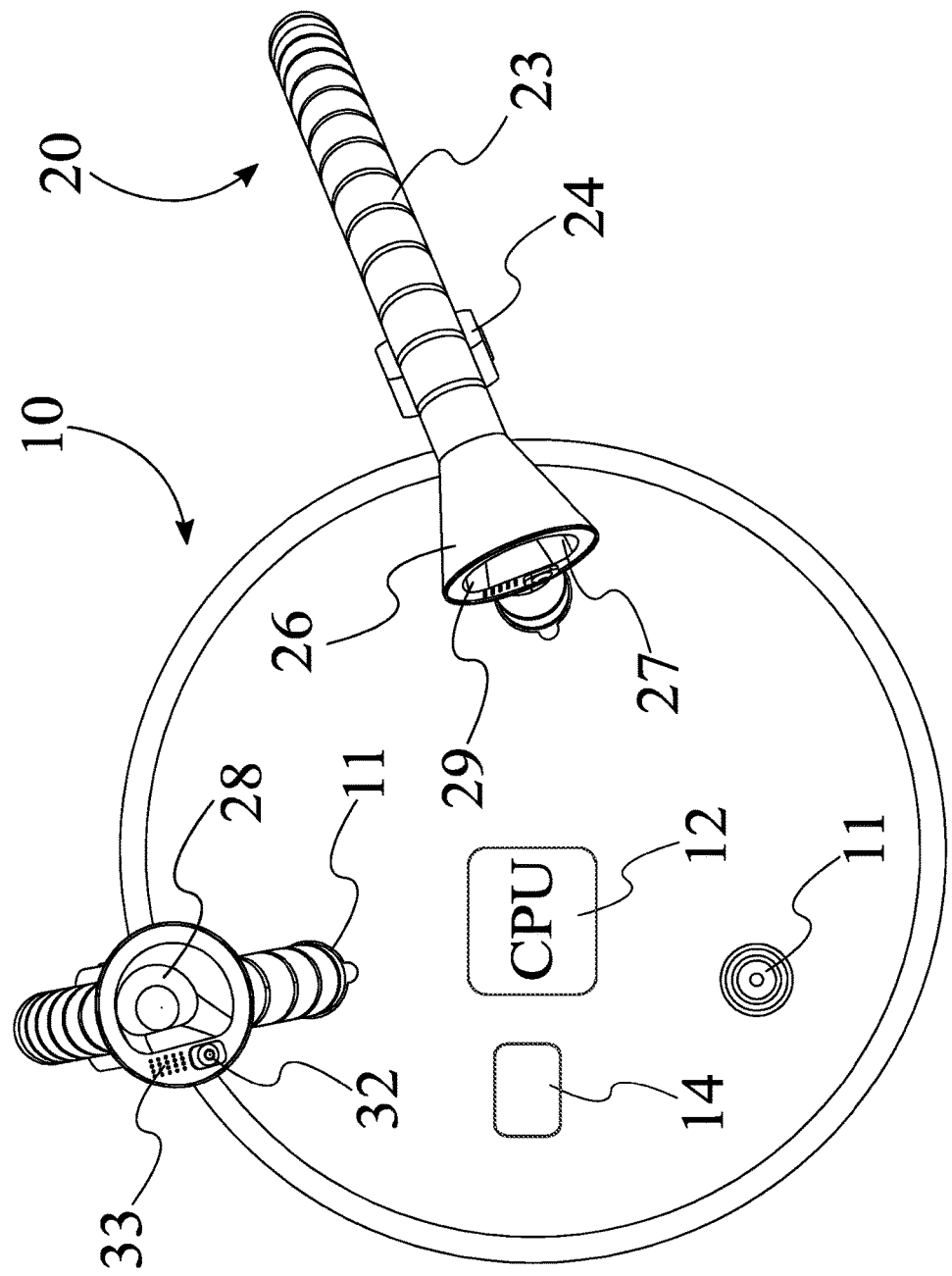
FIG. 6 is a bottom view of the present invention, wherein a speaker is observed adjacent with a camera. Further observed is an optional tab of the base jack on an individual illumination arm and a third port is observed unoccupied.

As can be seen in FIG. 6, the processor 12 of the base 10 is housed arbitrarily within the base 10 and in connection to the plurality of cables 13. Specifically, the processor 12 executes the functions and interprets the data of the microphone 25, the camera 32, the speakers 33, and the illumination head 26. Additionally, the processor 12 may comprise a relay 14 therein that permits the lighting system to facilitate wireless communications with an extraneous PC device 16 or any other device such as a display. The relay 14 is attached to the base 10 adjacent the processor 12. Spanning through the body in connection between the processor 12 and the jack 21 of the at least one illumination arm 20, and further between the processor 12 and an extraneous power grid of the particular facility is the plurality of cables 13. The plurality of cables 13 facilitates the transmission of power and information therethrough. Additionally, the plurality of cables 13 may further comprise a disparate number of diameters therebetween where thinner cables are employed within the base 10 and thicker cables are employed between the base 10 and the extraneous ceiling, wall, or fixture. The power source 17 is mounted within the base 10 and connected to both the processor 12 and the relay 14. The at least one illumination arm 20 is coupled with the base 10 through the jack 21 and an individual port of the plurality of ports 11, wherein the at least one illumination arm 20 may comprise a count up to the count of the plurality of ports 11. Additionally, the at least one illumination arm 20 comprises a plurality of wires that span along the arm 21 to the illumination head 26.

As can be seen in FIG. 1 to FIG. 5, the microphone 25 is attached to the arm 23 of the at least one illumination arm 20, arbitrarily between the jack 21 and the illumination head 26. Additionally, the microphone 25 is connected to the processor 12 and the power supply 17 of the base 10. The microphone 25 can be used by a user to intercept voice commands of the user and record audio data, comments, narratives through the relay 14 and processor 12 during the use of the present invention. As can be seen in FIG. 1 to FIG. 4, the arm 23 of the at least one illumination arm 20 comprises a handle 24, which is exteriorly attached to the arm 23 adjacent the illumination head 26 in the preferred embodiment or arbitrarily along the arm 23 between the microphone 25 and the illumination head 26 in alternative embodiments. The handle 24 allows the user to clasp the handle 24 to direct the illumination head 26 to any arbitrary orientation.

As can be seen in FIG. 6, the arm 21 is disposed between the jack base 22 and the illumination head 26 is the arm 23. Wherein the arm 23 preferably comprises a malleable stem that facilitates direction of the illumination head 26 in a particular direction and orientation. The arm 23 further comprises a cavity along the length thereof with the plurality of wires therethrough that connects the jack 21 with the microphone 25, the camera 32, and the speaker 33. The arm 23 may comprise an arbitrary length that may suit the situation and the at least one illumination arm 20 may be removed modularly from the base 10 and replaced with a longer or shorter individual arm 23. Located at one distal end of the individual illumination arm 20 is the jack 21, wherein the jack 21 engages with the individual port of the plurality of ports 11 on the base 10. The jack 21 couples the at least one illumination arm 20 with the base 10, facilitating the transmission of power and information therebetween. The jack 21 preferably is plugged into the individual port of the plurality of ports 11, although other electrical coupling means may be employed such as, but not limited to, USB jacks, power couplers, prongs, and so on. Additionally, the jack 21 of the at least one illumination arm 20 comprises a jack base 22 which is interstitially located between the arm 23 and the jack 21. The jack base 22 comprises a tab or similar to facilitate removal of the at least one illumination arm 20 from the base 21. The jack base 22 may further employ a self-locating geometry that locks the jack 21 into the individual port of the plurality of ports 11 through rotation therein. Through reversing rotation, the at least one illumination arm 20 may be removed.

As can be seen in FIG. 6, the illumination head 26 of the at least one illumination arm 20 comprises an illumination recess 27, an illumination means 28, an illumination cover 29, and a plurality of illumination apertures 31. The camera 32 and speaker 33 of the at least one illumination arm 20 are exteriorly on the illumination head 26. Disposed at the second distal end of the arm 23 opposite the jack 21 and jack base 23 is the illumination head 26. The illumination means 28 is enclosed within the illumination recess 27 of the illumination head 26. The illumination head 26 further comprises the plurality of wires spanning therethrough that connect the illumination means 28, the speaker 33, and the camera 32 with the jack 21. The illumination head 26 may further optionally facilitate swiveling about the distal end of the arm 23. Located at the distal end of the illumination head 26 opposite the arm 23 is the illumination recess 27, whereupon the illumination means 28 is housed therein and opens outward opposite from the arm 23. The illumination recess 27 may accommodate therein optional reflective coating or mirrors about the lateral walls to intensify the light in a particular direction or magnitude. Housed within the illumination recess 27 and disposed on the inner-most planar surface is the illumination means 28. The illumination means 28 facilitates illumination therefrom such as by a bulb, LED, filament, or similar that is connected to the jack 21 through the plurality of wires. Located on the distal end of the illumination head 26 opposite the arm 23 is the illumination cover 29, wherein the illumination cover 29 is preferably transparent and may optionally be removable from the illumination head 26 to replace the illumination means 28 within the illumination recess 27. The illumination cover 29 may further possess a plurality of apertures 31 that facilitates transmission of sound and images between the environment, the camera 32, and the speaker 33. Disposed on the distal surface of the illumination head 26 opposite the arm 23 is the camera 32. Wherein the camera 32 is accommodated by the planar surface of the illumination head 26 shared by the speaker 33 and the illumination recess 27. The camera 32 is in connection to the jack 21 through the plurality of wires spanning through the arm 23. The camera 32 may be engaged autonomously, remotely, or by voice command and thereafter capturing video or images in the orientation that the illumination head 26 is directed to. Further disposed on the distal planar surface of the illumination head 26 shared with the camera 32 is the speaker 33. The speaker 33 is exteriorly positioned on the illumination head 26 and in connection to the jack 21 through the plurality of wires spanning through the arm 23. The speaker 33 may output sound, music, and engage in communication between an extraneous PC device 16 of the base 10, when the at least one illumination arm 20 is engaged with the base 10, connecting the jack 21 to the processor 12.

The flexible lighting system of the present invention further comprises a cover 40, which comprises a cover fastener 41 and a front end 42. The cover 40 may be attached over the individual arm of the at least one illumination arm 20. In the preferred embodiment of the present invention, the front end 42 of the cover 40 is positioned on the cover 40 adjacent the illumination head 26 of the at least one illumination arm 20 and may be a transparent or translucent end that facilitates transmission of illumination and vision therethrough. Additionally, the cover 40 may be disposable and is generally tubular in shape. Located preferably along the rim of the cover 40 is the cover fastener 41 that facilitates the attachment of the cover 40 to the arm 23 of the at least one illumination arm 20. More specifically, the cover fastener 41 is exteriorly positioned on the cover 40 to seal the at least one illumination arm 20 within the cover 40. Thus, the cover fastener 41 mitigates the removal of the cover 40 until engaged by the user to remove. Preferably, the cover fastener 41 comprises a clamp or clipping means that couples to the arm 23, although other cover fastening means may be employed including, but not limited to, elastic apertures and bands, snap fits, and so on. Further, the cover fastener 41 may necessitate a complementing cover fastening means on the arm 23.

Figure 7:
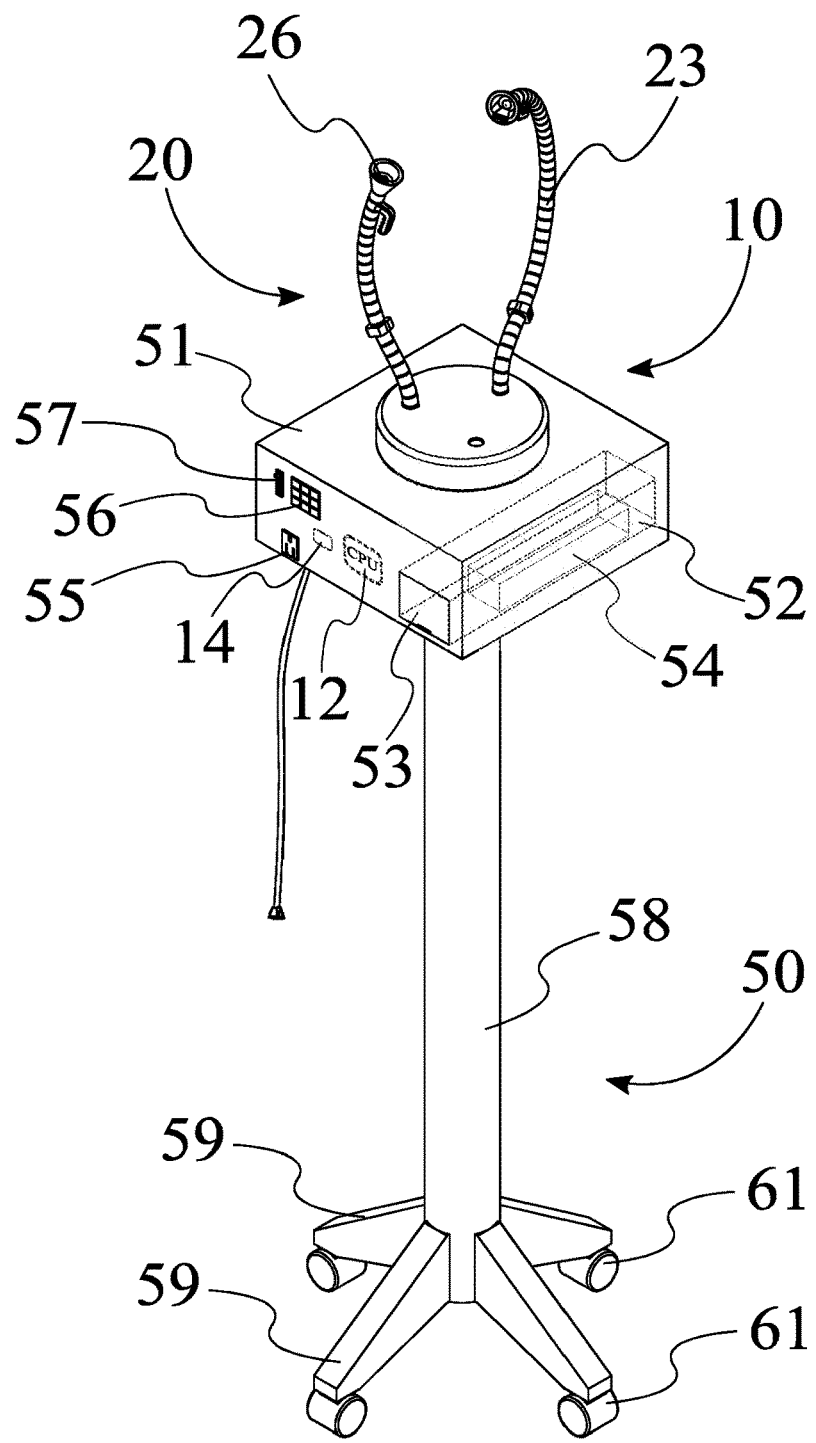
FIG. 7 is a perspective view of the mobile embodiment of the present invention, wherein a stand with a plurality of wheels supporting the lighting device of the present invention is observed with a stand casing being underneath the base that is now vertically reversed.
Figure 8:
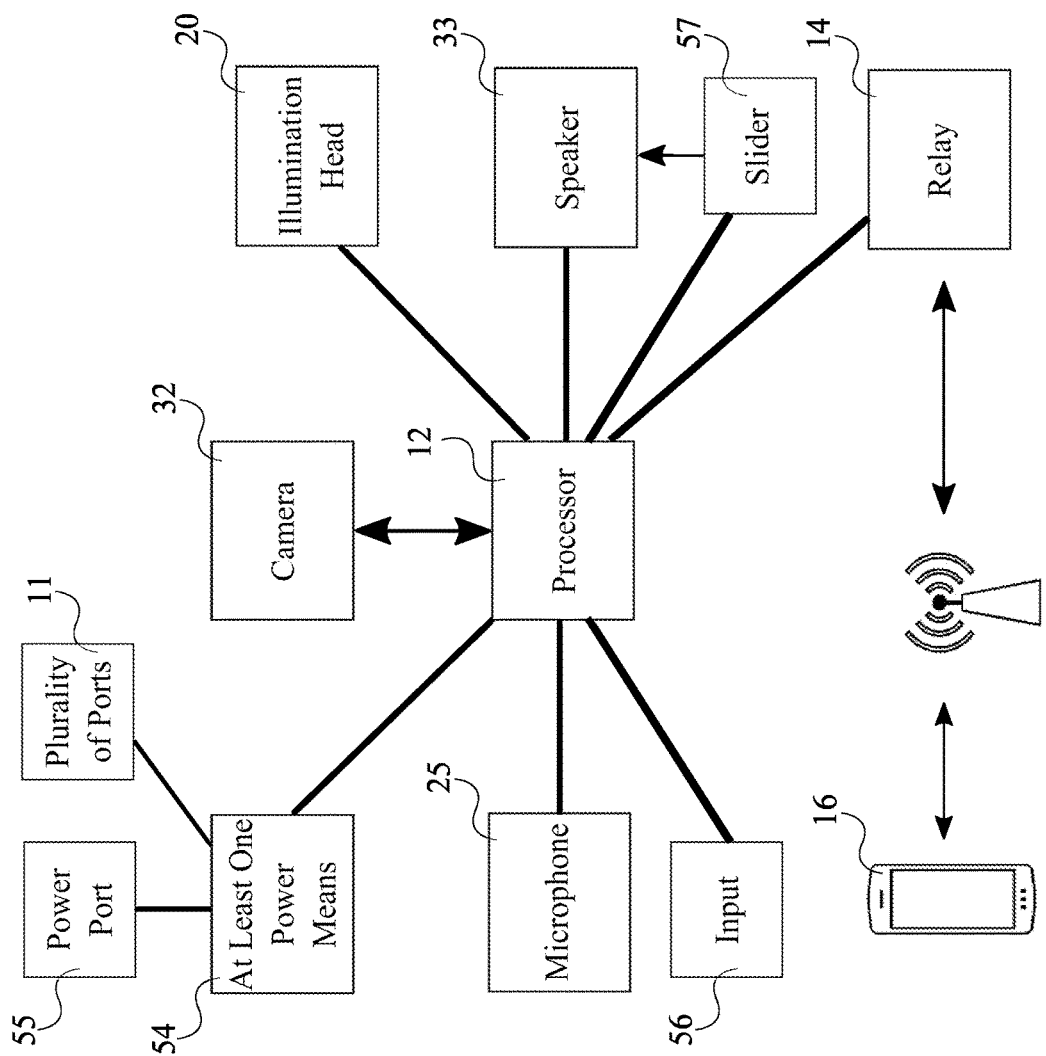
FIG. 8 is an electrical diagram of the lighting system of the present invention.

As can be seen in FIG. 7, the lighting system of the present invention comprises a stand 50. The stand 50 comprises a stand casing 51, a column 58, a plurality of legs 59, and a plurality of wheels 61. The stand casing 51 is distally and terminally attached to the column 58. The plurality of legs 59 is distally and terminally attached to the column 58 opposite the stand casing 51. Additionally, the plurality of legs 59 is perimetrically distributed on the column 58 and each of the plurality of wheels 61 is terminally attached to one of the plurality of legs 59. Further, the base 10 is exteriorly mounted to the stand casing 51 opposite the column 58 of the stand 50. Located atop the column 58 of the stand 50 is the stand casing 51. The stand casing 51 comprises the stand casing comprises a power storage enclosure 52, at least one power means 54, at least one power port 55, at least one input 56, and at least one slider 57. The power storage enclosure 52 is positioned inside the stand casing 51 and comprises a detachable enclosure door 53. The detachable enclosure door 53 is mounted on and flush with the exterior surface of the base 10. The at least one power means 54 is detachably mounted to the interior of the power storage enclosure 52. The at least one power port 55 is mounted to and flush to the exterior surface of the stand casing 51. Both the at least one input 56 and the at least one slider 57 are mounted to the exterior surface of the stand casing 51 adjacent the at least one power port 55. The at least power port 55 is electrically connected to the at least one power means 54. The at least one input 56 is electrically connected to the at least one power means 54. The at least one slider 57 is electrically connected to the at least one power means 54, and the at least one slider 57 is electrically connected to the illumination head 26 of the at least one illumination arm 20, as can be seen in FIG. 8.

Preferably the stand casing 51 comprises a cubic rectilinear profile with planar lateral walls and a planar top surface that the base 10 rests upon. The stand casing 51 is further preferably hollow, accommodating the power storage enclosure 52, the at least one power means 54, the at least one power port 55, the at least one input 56, and the at least one slider 57 on the exterior and the interior of the stand casing 51. Preferably located along one of the lateral walls of the stand casing 51 at an arbitrary height thereof is the power storage enclosure 52. The power storage enclosure 52 is recessed within the stand casing 51 and houses the at least one power means 54 therein. The power storage enclosure 2 is preferably rectilinear in profile and associated to the lateral wall of the stand casing 51 by a hinge on the enclosure door 53, thus allowing the power storage enclosure 52 to be opened and closed, exposing the at least one power means 54 therein. However other power enclosures may be employed including, but not limited to, sliding panels, snap fitting panels, and so on. The stand casing 51 may further comprise the processor 12, the relay 14, and the PC device 16. The relay 14 is exteriorly attached to the stand casing 51. The processor 12 attached to stand casing 51 adjacent the relay 14. The processor 12 is electrically connected to the relay 14, the at least one input 56, the at least one power means 54, and both the speaker 32 and the camera 33 of the at least one illumination arm 20. Further, the processor 12 is connected to the PC device 16 through the relay 14 over an external communication network.

As can be seen in FIG. 7, the at least one power means 54 is preferably housed within the power storage enclosure 52. The at least one power means 54 may comprise either a battery, a wall outlet cable, or multiple power means. The processor 12 of the base 10 may regulate the use of energy from the at least one power means 54. Further, the at least one power means 54 may facilitate recharging where two or more power means are employed by the present invention, whereupon the processor 12 regulates the distribution of electrical power. Disposed preferably upon one of the lateral walls of the stand casing 51 shared by the power storage enclosure 52 is the at least one power port 55. The at least one power port 55 preferably comprises an outlet that an AC (alternating current) cord may plug into, drawing power for an extraneous device from the at least one power means 54.

Further preferably disposed along one of the lateral walls of the stand casing 51, shared by the power storage enclosure 52 and the at least one power port 55 is the at least one input 56, which may be electrically connected with components including, but not limited to, the microphone 25, the camera 33, etc., of the at least one illumination arm 20. The user may engage to control the functionality of the at least one illumination arm 20 regarding light control, intensity, and activation of the speaker 33, microphone 25, and/or camera 32. Preferably the at least one input 56 comprises a depressible key or a plurality thereof in a keypad configuration. The at least one input 56 may further be embodied by a touchscreen controller to facilitate similar commands. Further disposed along a lateral wall coincident with and adjacent to the at least one input 56 is the at least one slider 57. The at least one slider 57 may facilitate a switching state consequent to the tiers of the slider, or an analog slider to vary the intensity of the illumination means 28 of the at least one illumination arm 20 and the speaker 33. Protruding beneath the stand casing 51 and above the plurality of legs 59 is the column 58. The column 58 raises the stand casing 51 an arbitrary height above the ground. Additionally, the column 58 may comprise a telescoping column or pin lock to adjust the height of the column 58. Located near the bottom of the column 58 and preferably protruding from the longitudinal surfaces of the column 58 is the plurality of legs 59. The plurality of legs 59 preferably protrudes outward from the center of the column 58 and rest atop a plurality of wheels 61. Connected to the plurality of legs 58 and preferably in a count equivalent thereto is the plurality of wheels 61. The plurality of wheels 61 facilitates mobility of the stand 50. Optionally, the plurality of wheels 61 may individually comprise wheel locks that arrest rotation, thus arresting the motion of the stand 50.

Although the invention has been explained in relation to its preferred embodiment, it is to be understood that many other possible modifications and variations can be made without departing from the spirit and scope of the invention as hereinafter claimed.

What is claimed is:

1. A flexible lighting system for medical, dental, and veterinary facilities comprising:
    a base;

at least one illumination arm;

a stand;

the base comprising a plurality of ports and a plurality of cables;

the plurality of ports being terminally positioned on the base;

the plurality of cables being terminally positioned on the base opposite the plurality of ports;

the at least one illumination arm comprising a jack, an arm, and an illumination head;

the illumination head being terminally positioned on the arm;

the jack being terminally positioned on the arm opposite the illumination head;

the jack being mounted to one of the plurality of ports of the base;

the at least one illumination arm being detachably attached to the base through the jack;

the illumination head of the at least one illumination arm being connected to an external power source through the plurality of cables of the base;

the stand comprising a stand casing, a column, a plurality of legs, and a plurality of wheels;

the stand casing being distally and terminally attached to the column;

the plurality of legs being distally and terminally attached to the column opposite the stand casing;

the plurality of legs being perimetrically distributed on the column;

each of the plurality of wheels being terminally attached to one of the plurality of legs;

the base being exteriorly mounted to the stand casing opposite the column;

the stand casing comprising a power storage enclosure, at least one power means, at least one power port, at least one input, at least one slider;

the power storage enclosure being positioned inside the stand casing;

the power storage enclosure comprising a detachable enclosure door;

the detachable enclosure door being mounted on and flush with the exterior surface of the base;

the at least one power means being detachably mounted to the interior of the power storage enclosure;

the at least one power port being mounted to and flush to the exterior surface of the stand casing;

both the at least one input and the at least one slider being mounted to the exterior surface of the stand casing adjacent the at least one power port;

the at least power port being electrically connected to the at least one power means;

the at least one input being electrically connected to the at least one power means;

the at least one slider being electrically connected to the at least one power means;

the at least one slider being electrically connected to the illumination head of the at least one illumination arm; and the at least one input being electrically connected with the microphone of the at least one illumination arm.

2. The flexible lighting system for flexible lighting system for medical, dental, and veterinary facilities as claimed in claim 1 comprising:

the at least one illumination arm comprising a microphone; and microphone being attached to the arm between the illumination head and the jack.

3. The flexible lighting system for medical, dental, and veterinary facilities as claimed in claim 1 comprising:

the at least one illumination arm comprising a camera and a speaker; and both the camera and the speaker being exteriorly positioned on the illumination head.

4. The flexible lighting system for medical, dental, and veterinary facilities in claim 1 comprising:

the at least one illumination arm comprising a handle;

the handle being exteriorly attached to the arm; and the handle being positioned adjacent the illumination head.

5. The flexible lighting system for medical, dental, and veterinary facilities in claim 1 comprising:

the base comprising a processor, a relay, a power source, and an extraneous personal computing (PC) device;

the power source being mounted within the base;

both the processor and the relay being attached to the base;

both the processor and the relay being connected to the power source; and the PC device being connected to the processor through the relay and a communication network.

6. The flexible lighting system for medical, dental, and veterinary facilities in claim 1, wherein the base is configured to be installed on the existing light fixture bases.

7. The flexible lighting system for medical, dental, and veterinary facilities as claimed in claim 1, wherein the at least one input comprising a touchscreen controller.

8. The flexible lighting system for medical, dental, and veterinary facilities as claimed in claim 1 comprising:

the stand casing comprising a processor, a relay, and a PC device;

the relay being exteriorly attached to the stand casing;

the processor being attached to stand casing adjacent the relay;

the processor being electrically connected to the relay;

the processor being electrically connected to the at least one input;

the processor being electrically connected to the at least one power means;

both the speaker and the camera of the at least one illumination arm being electrically connected to the processor; and the processor being connected to the PC device through the relay over an external communication network.

\* \* \* \* \*